United States Patent [19]

Mizuno

[11] Patent Number: 6,047,083

[45] Date of Patent: Apr. 4, 2000

[54] METHOD OF AND APPARATUS FOR PATTERN INSPECTION

[75] Inventor: Fumio Mizuno, Tokorozawa, Japan

[73] Assignee: Hitachi, Ltd., Tokyo, Japan

[21] Appl. No.: 09/013,913

[22] Filed: Jan. 27, 1998

[30] Foreign Application Priority Data

Jan. 29, 1997 [JP] Japan ................................. 9-014922

[51] Int. Cl.⁷ ................................................ G06K 9/00
[52] U.S. Cl. ............................ 382/141; 382/294; 348/87
[58] Field of Search ................................. 382/141, 149, 382/151, 150, 145, 144; 348/125, 126, 86, 87; 364/468.01, 468.02

[56] References Cited

U.S. PATENT DOCUMENTS 5,544,256   8/1996   Brecher et al. ........................ 382/149
5,801,965   9/1998   Takagi et al. ........................... 702/35

*Primary Examiner*—Amelia Au
*Assistant Examiner*—Vikkram Bali
*Attorney, Agent, or Firm*—Antonelli, Terry, Stout & Kraus, LLP

[57] ABSTRACT

A method and apparatus for pattern inspection forming an image of a specimen and inspecting a pattern formed on the specimen. This method includes the steps of storing a reference image corresponding to an image of the specimen into a memory, comparing the read out reference image from the memory with the image of the specimen, detecting differing portions between the reference image and image of the specimen as defects, and determining a probability of defects being or becoming a killer defect (i.e., a defect causing failure) of the specimen from other defects based on the detected differing portions.

3 Claims, 10 Drawing Sheets

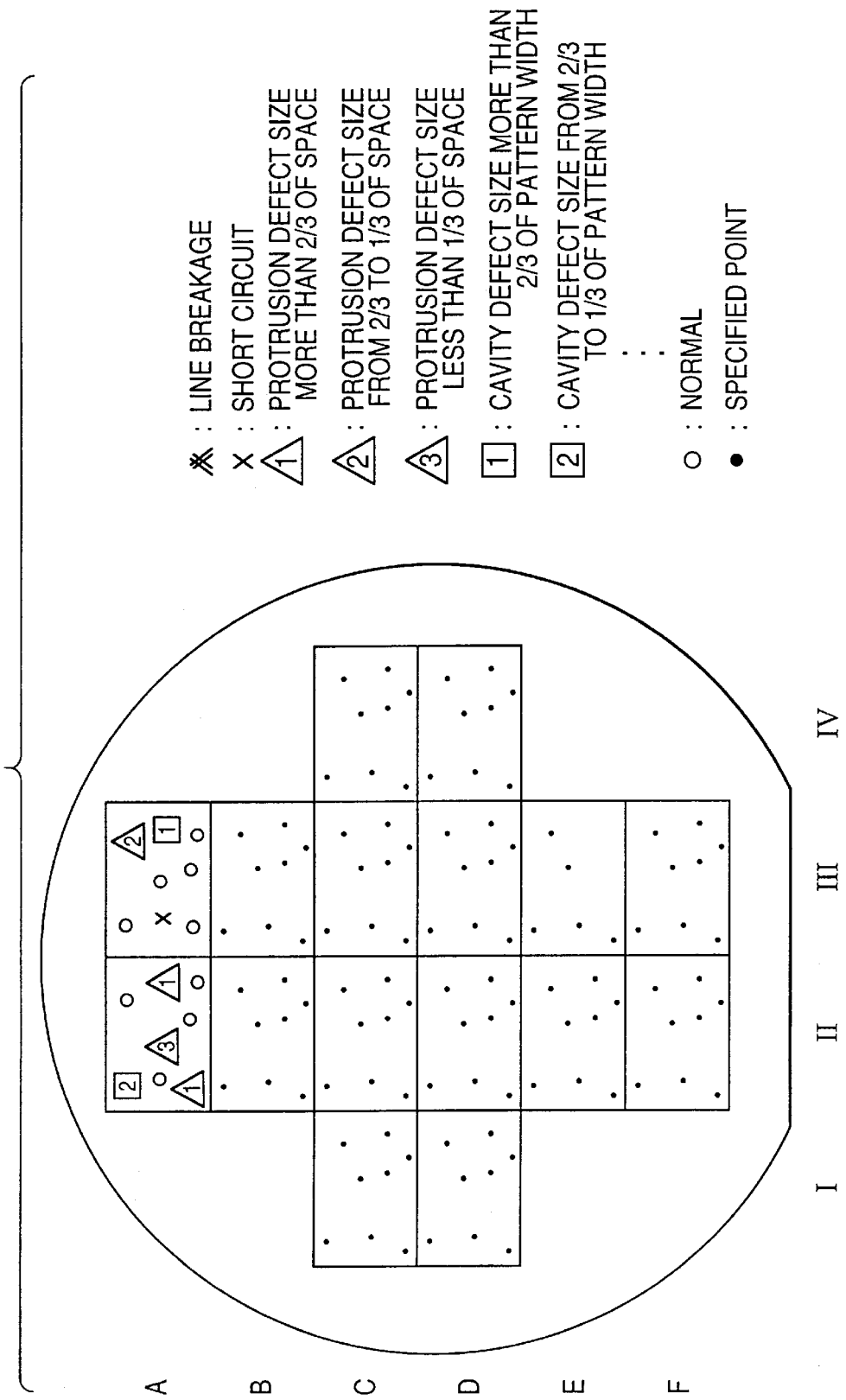

FIG. 7

| TYPE OF DEFECT | | CHIP NUMBER | A II | A III | B II | ... | DENSITY OF DEFECT WITHIN A WAFER |
|---|---|---|---|---|---|---|---|
| LINE BREAKAGE | | | 0 | 0 | ... | ... | 0/16 |
| SHORT CIRCUIT | | | 0 | 1 | ... | ... | 1/16 |
| PROTRUSION DEFECT | SIZE MORE THAN 2/3 OF SPACE | | 2 | 0 | ... | ... | 2/16 |
| | SIZE FROM 1/3 TO 2/3 OF SPACE | | 0 | 1 | ... | ... | 1/16 |
| | SIZE LESS THAN 1/3 OF SPACE | | 1 | 0 | ... | ... | 1/16 |
| CAVITY DEFECT | SIZE MORE THAN 2/3 OF PATTERN WIDTH | | 0 | 1 | ... | ... | 1/16 |
| | SIZE FROM 1/3 TO 2/3 OF PATTERN WIDTH | | 1 | 0 | ... | ... | 1/16 |
| | SIZE LESS THAN 1/3 OF PATTERN WIDTH | | 0 | 0 | ... | ... | 0/16 |
| PINHOLE DEFECT | ... | ... | ... | ... | ... | ... | ... |
| ISOLATION DEFECT | ... | ... | ... | ... | ... | ... | ... |
| NO DEFECT (NORMAL) | | ○ | 4 | 5 | | | 9/16 |
| DENSITY OF DEFECT WITHIN A CHIP | | | 4/8 | 3/8 | | | |

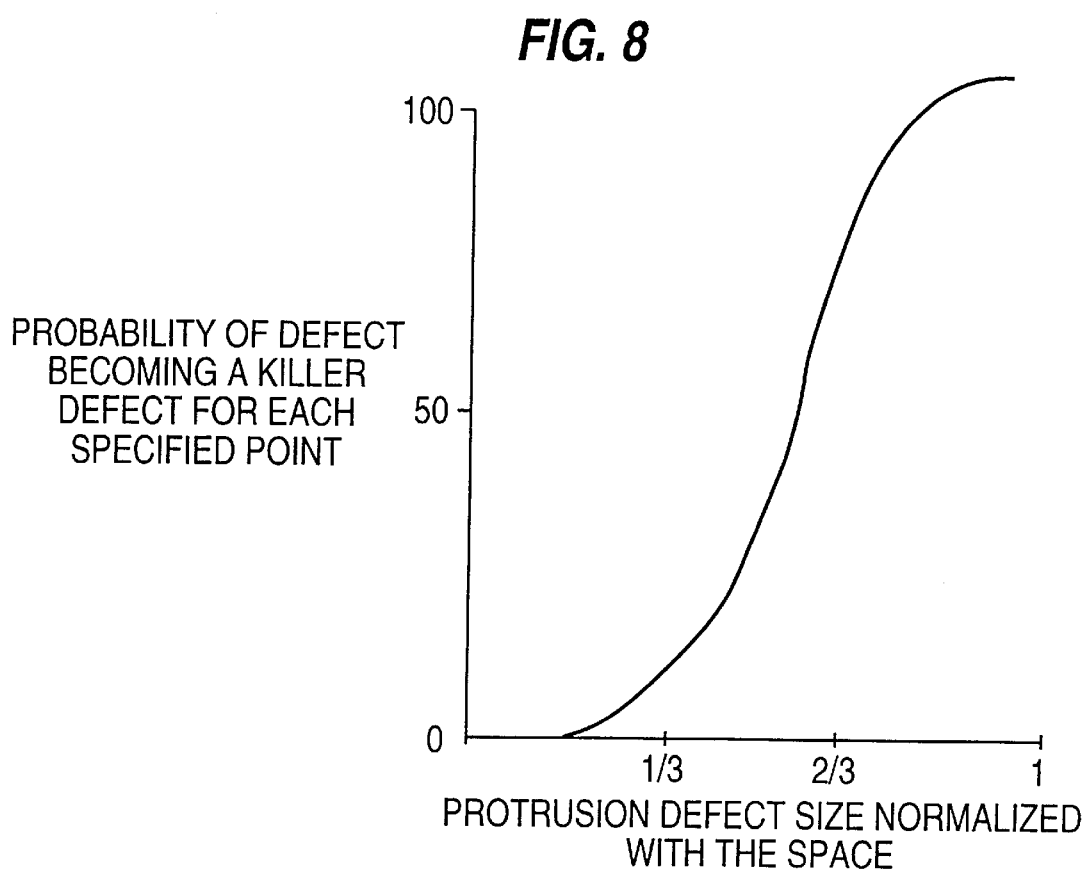

PROBABILITIES OF INDIVIDUAL CHIPS DEVELOPING
KILLER DEFECTS IN FINAL PRODUCT

METHOD OF AND APPARATUS FOR PATTERN INSPECTION

BACKGROUND OF THE INVENTION

The present invention relates to a method of and an apparatus for pattern inspection as one of the indispensable technologies for formation of patterns used in various industrial fields including fabrication of semiconductor devices. In particular, it relates to an apparatus for pattern inspection in which an image is formed with the use of such a device as a scanning electron microscope (SEM for visual inspection), laser scanning microscope, i-beam microscope, and scanning atomic force microscope and the pattern is inspected by observing the thus formed image.

One typical field of application of the present invention is the area of semiconductor manufacturing. In semiconductor manufacturing, the visual-inspection SEM (scanning electron microscope) is widely used for pattern inspection. Inspection of a pattern form with the use of a visual-inspection SEM is carried out, for example, through the following steps.

A sheet of wafer to be inspected, which has been taken out from a wafer cassette, is subjected to a pre-alignment process with an orientation flat portion or notch of the wafer used as a reference. Pre-alignment is a process to align the crystalline direction of the wafer in the moving direction of an XY-stage. After pre-alignment, the wafer is transported to and mounted on the XY-stage and placed in a specimen chamber which is kept in a vacuum. The wafer mounted on the XY-stage is then subjected to an alignment process with the use of an optical microscope mounted on the top of the specimen chamber. This alignment process is used to adjust the coordinate system of the pattern formed on the wafer to the coordinate system of the stage. To be more specific, the alignment is performed by comparing an image of the alignment pattern formed on the wafer magnified several hundred times by the optical microscope with a previously recorded reference image of the alignment pattern, and adjusting the positional coordinates of the stage so that the former image correctly registers with the latter, reference image. After the alignment, the wafer is shifted to a desired point to be inspected by movement of the stage. The point to be inspected is moved to the position irradiated by the scanning electron beam and thereby an SEM image is formed. The operator observes the formed SEM image based on the knowledge and information the operator has, and makes determinations as to the existence of pattern defects and defect classification.

The method mentioned above is defect classification in terms of the operator's vision. On the other hand if the object is converted to an optical microscopic image instead of a SEM image, an automatic classification is performed. This method of automatic classification is such that after extracting characteristics such as size and shape from the obtained defect image, a defect classifier performs an automatic classification based on the characteristics. For this purpose, a classifier such as neural network is in popular use. Such a method is disclosed in M. H. Bennett, "Automatic Defect Classification: Status and industry trends", pp. 210–220, Proceedings of SPIE, Vol. 2439, 1995, which is hereby incorporated by reference.

The main purpose of the defect classification is to accurately determine the existence of defects severe enough to cause failures in the devices (a so-called "killer defect") and to sort them out. By determining these killer defects, it becomes possible to effectively decrease defects affecting the product yield and thereby improve the product yield in a short period of time.

By Convention, defect classifications have generally been made by representing them by their geometric forms such as circles, squares, rectangles, and triangles or describing the sizes of the defects in absolute measures. Such ways of classification, however, have not always been suitable ways to segregate killer defects from non-killer defects.

SUMMARY OF THE INVENTION

An object of the present invention is to provide an apparatus for pattern inspection suited for accurately and quickly determining the existence of killer defects and classifying the defects.

The present invention, in an apparatus for pattern inspection producing an image of a specimen and inspecting the pattern formed on the specimen, is characterized in that it is configured to put a reference image corresponding to the image of the specimen into storage, to read the reference image out of the storage, to compare the read out reference image with the image of the specimen, to detect portions at which both the images differ from each other, and to segregate killer defects from other defects based on the detected portions.

According to the present invention, an apparatus and method for pattern inspection suited for determining the existence of killer defects accurately and quickly and classifying them can be provided.

BRIEF DESCRIPTION OF THE DRAWINGS

FIGS. 6A and 6B are drawings explanatory of displaying specified points to be inspected and the result of the defect classification in accordance with the present invention;

FIG. 7 is a table explanatory of calculation of the probability of defect occurrence in accordance with the present invention;

FIG. 8 is a drawing explanatory of the correlation between the degree of criticalness and protrusion defect size in accordance with the present invention.

DESCRIPTION OF THE PREFERRED EMBODIMENTS

Figure 2A:
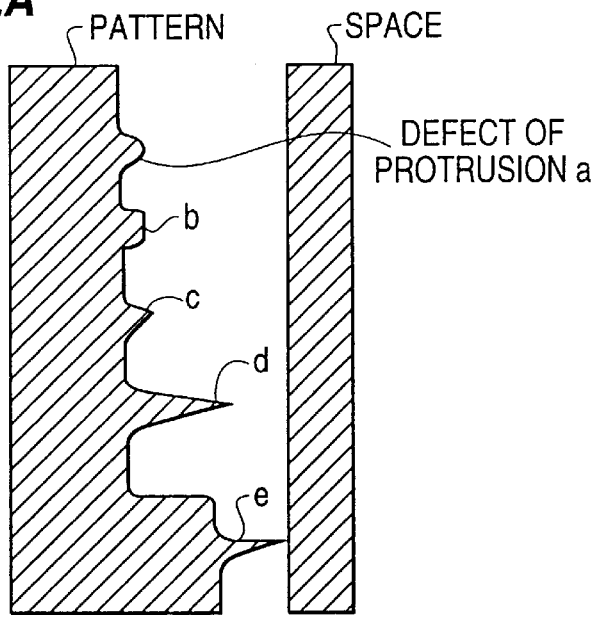
FIGS. 2A to 2D are drawings explanatory of defect classification in accordance with the present invention.

When, by way of the examples shown in FIG. 2A, the defects of protrusion in a wiring pattern are considered, it has been determined from experience that the rate of criticalness (i.e., the probability of a defect becoming a "killer defect", that is, a defect that definitely causes chip or wafer failure) of the defects has a lower correlation with their geometric forms and the absolute magnitude of the defects, as indicated by the defects a, b, and c, than the correlation of the relative magnitude between the defects and the space in the pattern, as indicated by the defects d and e. In other words, for defects a, b and c, the probabilities of the defects becoming killer defects are virtually the same, and are not dependent on their geometric form. On the other hand, the probability of the defect e becoming a killer defect is higher than the probability of d becoming a killer defect, even though d is larger than e.

Figure 2B:
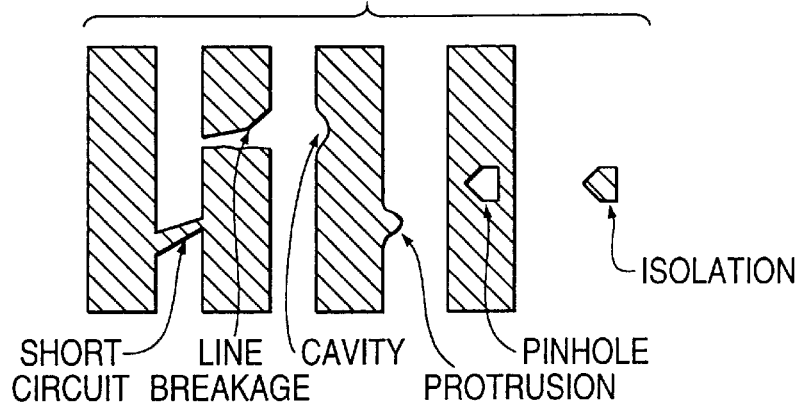

Further, as shown in FIG. 2B, a short circuit or line breakage in a wiring certainly becomes a "killer defect" regardless of the shape or size of the defective portion. Meanwhile, defects of protrusion, cavity, pinhole, and isolation can be mentioned as other defects similar to the defects of short circuit and line breakage. On the other hand, it is seldom that such defects as protrusion, cavity, pinhole, and isolation directly cause a failure. However, it is possible that such defects can lead to a failure later in the processing, a deterioration in the characteristic of the device, or a lowering of the reliability in the following steps.

Figure 2C:
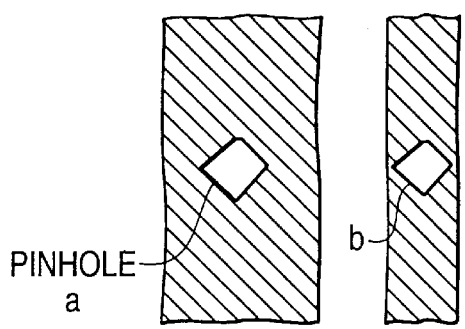
Figure 2D:
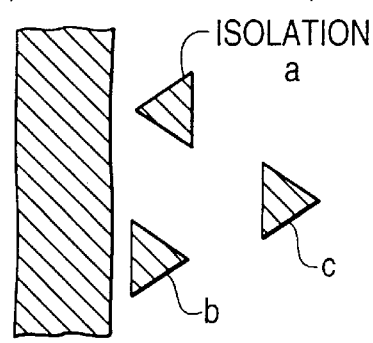

The probability of such a defect as a protrusion, cavity, pinhole, and isolation leading to a failure depends on the pattern size of the portion in which the defect is present and the distance to an adjoining pattern. Even with similar defects, the larger the pattern size of the portion in which the defect is present, or the larger the distance to the adjoining pattern, the less likely it is that the defect will become a killer defect. For example, in FIG. 2C, the probability of the pinhole b becoming a killer defect is greater than the probability that equally-sized pinhole a will become a killer defect because pinhole b is formed in a narrower pattern. Similarly, in FIG. 2D, the probabilities that the isolations shown there will become killer defects are greatest for defect b and lowest for defect c (with defect a in-between). Incidentally, the term "isolation" used herein refers to a type of defect such as shown in FIG. 2D where one or more isolated pieces of the material of the pattern are formed spaced apart from but adjacent to a portion of the pattern.

Upon investigation based on experience as described above, the method of inspection includes the step of classifying the defects at least into defects of a short circuit, line breakage, protrusion, cavity, pinhole, and isolation. Also, for the defects of protrusion, cavity, pinhole, and isolation, a further step is performed to sub-classify the defects by size with the pattern width or the space used as the unit. The apparatus for inspection is provided with a function to compare an image for inspection with a previously recorded reference image for inspection to detect a portion at which both the images differ from each other as a defect, and a function to classify the defects at least into types of defects of short circuit, line breakage, protrusion, cavity, pinhole, and isolation and, as for the defects of protrusion, cavity, pinhole, and isolation, to sub-classify them by size with the pattern width or the space used as the unit.

By the above described design, existence of killer defects can be determined more accurately and quickly and the defects can be classified.

Figure 1:
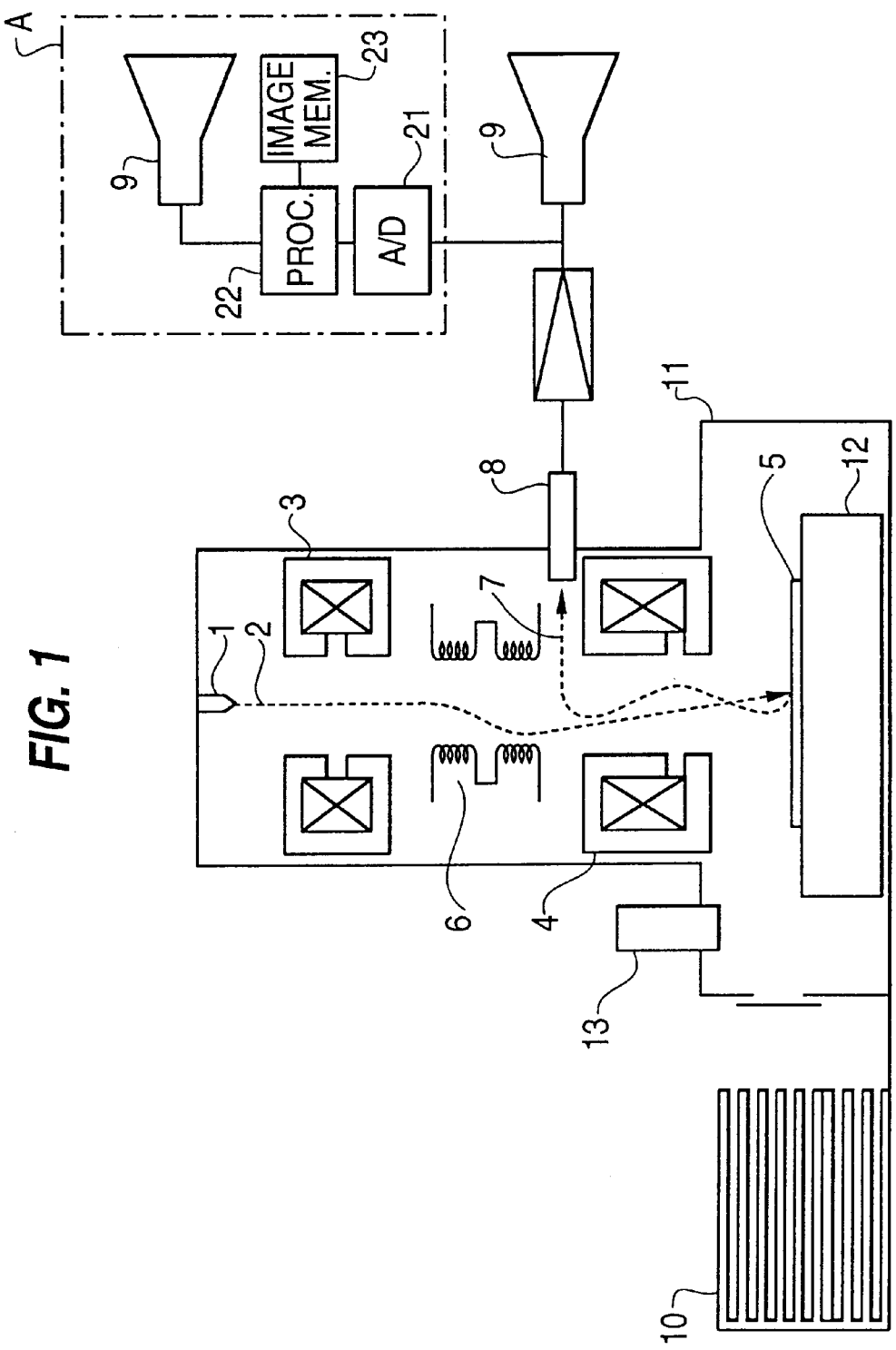
FIG. 1 is a general arrangement drawing of an embodiment of a visual-inspection SEM as an apparatus for pattern inspection according to the invention.

FIG. 1 shows a basic configuration of an embodiment of a visual inspection SEM as an apparatus for pattern inspection according to the present invention. An electron beam 2 emitted from an electron gun 1 is narrowed down by a focusing lens 3 and an objective lens 4 and focused on the face of a wafer 5 as a specimen. At the same time, the trajectory of the electron beam 2 is deflected by a deflector 6 and thereby the face of the wafer is scanned two-dimensionally.

Meanwhile, secondary electrons 7 are emitted from the portion of the wafer irradiated by the electron beam 2 and the secondary electrons 7 are detected by a secondary-electron detector 8 and turned into an electric signal, which is then subjected to such processes as amplification. The electric signal which has gone through these processes is used for luminance-modulating a display 9. Since the display 9 is scanned in synchronism with the scanning of the wafer face by the electron beam 2, an image of the specimen (SEM image) is formed on the display.

Figure 3:
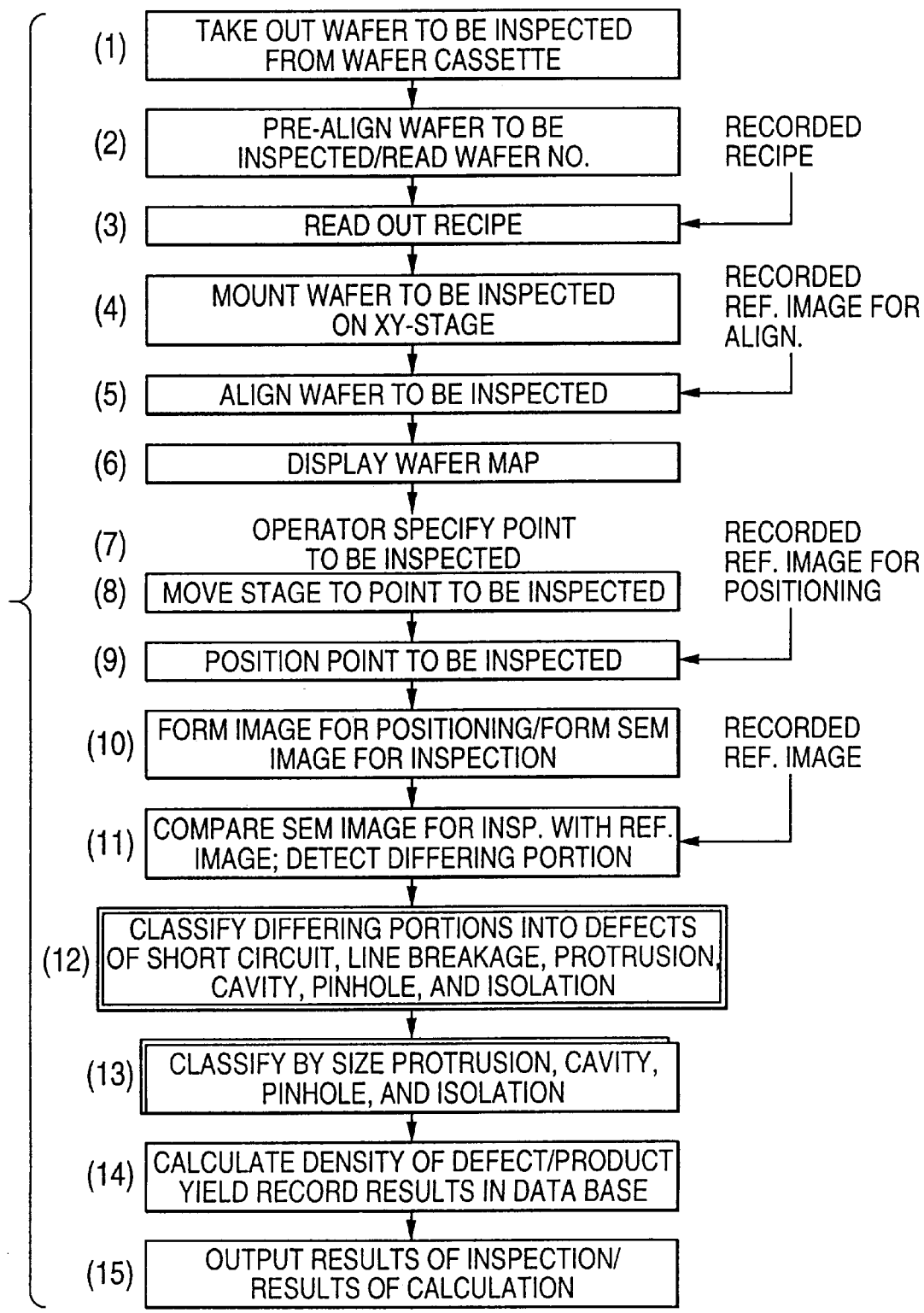
FIG. 3 is a flowchart explanatory of a procedure for inspection in accordance with the present invention.

An example of an inspecting procedure according to the invention is shown in FIG. 3. To begin, in step (1), one sheet of the wafer 5 to be inspected is taken out of a wafer cassette 10, as shown in step (1). In step (2), the wafer is subjected to a pre-alignment process and, at the same time, a wafer number formed on the wafer is read by a wafer number reader, not shown. The wafer number is uniquely assigned to each wafer. A previously recorded recipe corresponding to the wafer is read out with the read wafer number used as the key, as shown in step (3). The "recipe" is what provides the procedure for inspection of the wafer and conditions for the inspection.

The steps subsequent to the above are carried out automatically or semi-automatically in accordance with the read out recipe. After the wafer number has been read, the wafer 5 is transported to and mounted on an XY-stage 12 within a specimen chamber 11 held in a vacuum, shown in step (4). The wafer 5 mounted on the XY-stage 12 is then subjected to an alignment process by means of an optical microscope 13 mounted on the top of the specimen chamber 11, as shown in step (5). The alignment process is performed by comparing an optical microscopic image (magnified several hundred times) of the alignment pattern formed on the wafer 5 with a reference image for alignment previously recorded corresponding to the recipe, and adjusting the positional coordinates of the stage so that the former image registers with the latter, reference image. After the alignment has been made, a wafer map (a map of points to be inspected) corresponding to the wafer is read out and displayed on the display, as seen in step (6). The wafer map indicates the required points to be inspected of the wafer and their histories.

After the wafer map has been displayed, the operator specifies the point or points corresponding to one or more portions to be inspected out of the points which are displayed on the wafer map, as shown in step (7). When the point to be inspected has been specified, the wafer 5 is shifted by the movement of the stage so that the specified point to be inspected is brought precisely under the electron beam, as shown in step (8). After the wafer has been shifted, the specified point to be inspected is irradiated by the scanning electron beam and, thereby, a relatively lowly magnified SEM image (an image for positioning) is formed. The thus formed lowly magnified SEM image is compared, as was done in the alignment process, with a previously recorded reference SEM image (a reference image for positioning) corresponding to the specified point to be inspected, and precise positioning of the point to be inspected is performed such that the former image correctly registers with the latter, reference SEM image, as shown in step (9). The positioning is carried out, for example, by finely controlling the region scanned by the electron beam.

The wafer positioned as described above now has its region to be inspected located virtually in the center of the screen, i.e., precisely under the electron beam. In this state, a highly magnified SEM image for inspection (an image for inspection) of the region to be inspected is formed in step (10). The SEM image for inspection is compared with a reference SEM image (a reference image for inspection)

corresponding to the region under inspection recorded corresponding to the recipe, and the portion at which both the images differ from each other is detected in step (11). The differing portion is regarded as a pattern defect. The pattern defects are classified at least into types of defects of a short circuit, line breakage, protrusion, cavity, pinhole, and isolation in step (12).

Next, the defects of protrusion and isolation are classified by size by expressing the distance to the adjoining pattern with the minimum space used as the unit, and expressing the side-to-side length (the length of the shadow of the defect cast on the pattern) with the minimum pattern width used as the unit. On the other hand, the defects of pinhole and cavity are classified by size with the width of the pattern where the defect is present used as the unit in the lateral direction and with the minimum pattern width used as the unit in the longitudinal direction, as seen in step (13). Here, the minimum pattern width and the minimum space are values in accordance with the pattern designing rules of the device to be inspected and recorded prior to the inspection.

Figure 4:
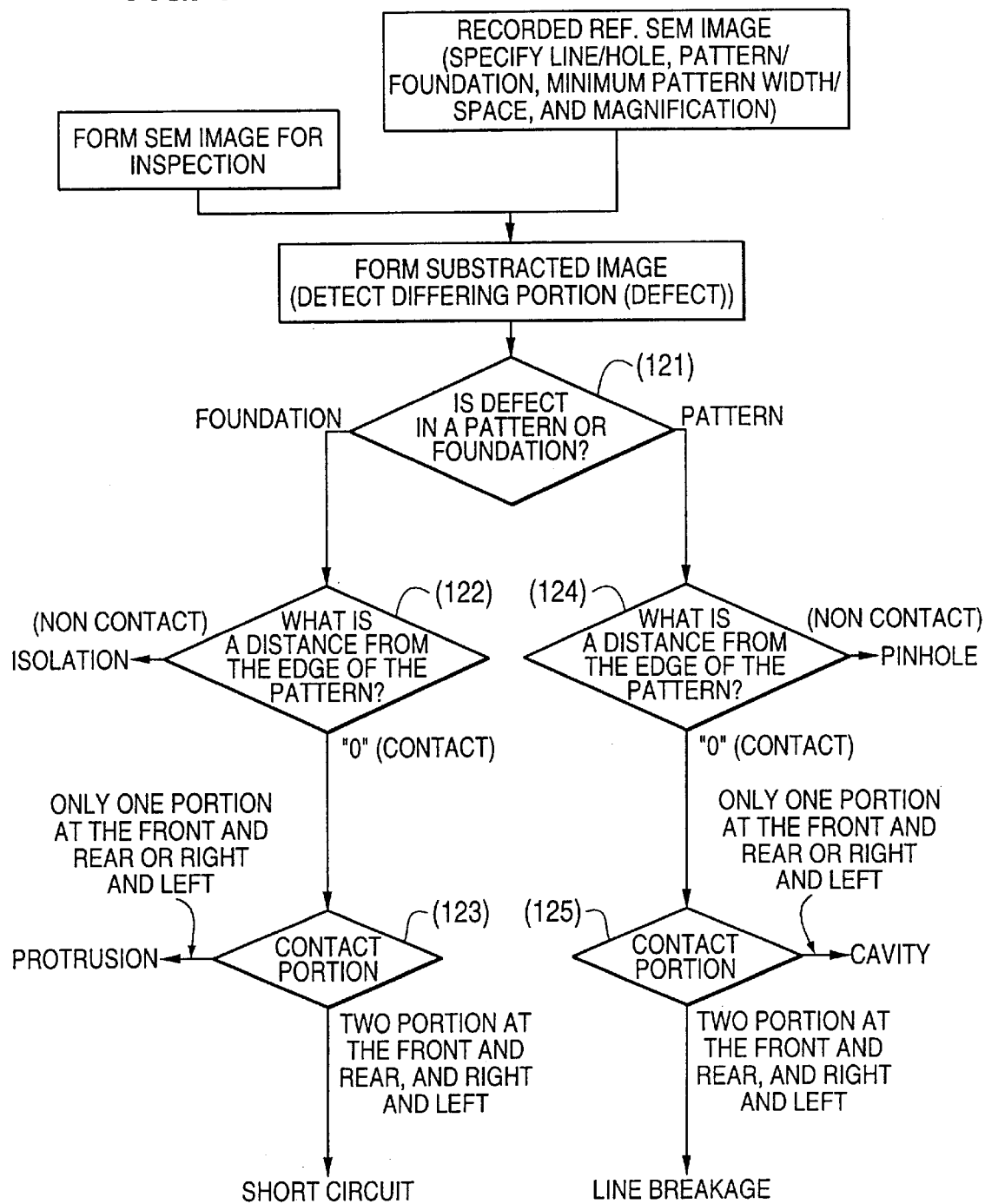
FIG. 4 is a flowchart explanatory of a procedure for type classification in accordance with the present invention.

The type classification of defects of step (12) is performed according to the procedure shown by the steps (124) to (125) in FIG. 4 as follows. When a previously prepared reference SEM image is recorded, the operator specifies line/hole, pattern/foundation, minimum pattern width/space, and magnification information for a pattern layer of the reference SEM image. After an SEM image for inspection is formed and the SEM image for inspection is compared with the reference SEM image and a differing portion, namely, a defect is detected, it is determined whether the defect is in the pattern or foundation based on a position of the defect in a display screen, as shown by step (121) in FIG. 4. If the defect is in the foundation, a distance between the defect and an edge of the pattern is calculated or measured as next step (122). This measurement in step (122) is performed according to one of the following two approaches 1) and 2):

1) The reference SEM image and a subtracted image obtained by the above comparing step are overlapped and displayed on the display screen, and then the subtracted image is shifted to the edge of the pattern so that the subtracted image comes into contact with the edge of the pattern, thereby, the distance between the defect and the edge of the pattern is obtained based on the distance of the movement; or 2) The reference SEM image and a subtracted image obtained by the above comparing step are overlapped and displayed with a predetermined scale on the display screen, and then the distance between the defect and the edge of the pattern is read by using the scale. This process which reads the distance is performed by the operator or a computer.

A method of a pattern matching is applied to the above first approach (1). The scale used in the above second approach (2) may be a concurrence of concentric circles which have an edge of the defect as the center of the circles or a grid line instead of a scale shaped like a straight line. As shown in step (122), if a distance between a defect and the edge of the pattern is not '0' and the defect does not contact with the edge of the pattern, the pattern defect is classified as an isolation.

On the other hand, if a distance between a defect and the edge of the pattern is '0' and the defect contacts with the edge of the pattern when the defect is shifted to the front and the rear or right and left, a contact portion where the defect contacted with the edge of the pattern is checked as the next step (123). If there is only one contact portion at the front and the rear or right and left, the pattern defect is classified as a protrusion. If there are two contact portion at the front and the rear or right and left, the pattern defect is classified as a short circuit.

If step (121) determines that the defects are in the pattern, the defects are classified as a pinhole, cavity, or line breakage with the same procedure, as shown in steps (124) and (125). In other words, step (124) utilizes the same approaches (1) and (2) performed in step (122) to determine whether the defect is a pinhole, and, if it is not, then step (125) is performed in a similar manner to step (123) to determine whether the defect is a cavity or line breakage.

Figure 5:
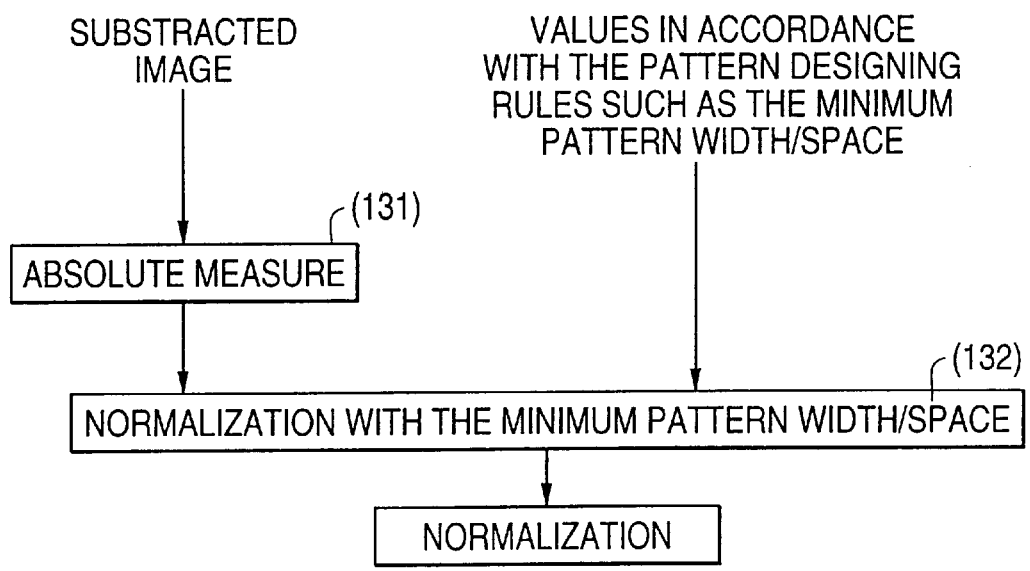
FIG. 5 is a flowchart explanatory of a procedure for size classification in accordance with the present invention.

After the type classification steps described above, the defects of protrusion, isolation, pinhole, and cavity are classified by size with the minimum pattern width and the minimum pattern space serving as the unit, as shown in step (13) of FIG. 3. The size classification of step (13) is performed according to the procedure shown in FIG. 5 as follows.

As a first step (131), a maximum absolute measure of the subtracted image (the defect) is obtained in each direction (X direction and Y direction) according to a well-known size measuring procedure using a critical dimensional scanning electron microscope (CD-SEM). Here, in the well-known size measuring procedure of the CD-SEM, an edge of a pattern is detected based on a line profile of the defect image, and the size of the pattern is obtained based on the distance between the edges of the pattern. The absolute measure obtained in above step (131) is normalized with values in accordance with the pattern designing rules of the device, such as the minimum pattern width/space specified when the previously reference SEM image is recorded, as shown in step (132).

The means used for classifying the types and sizes of the defects is, for example, of a hardware configuration such as shown in the portion A of FIG. 1. In other words, the elements shown in portion A carry out the above-described steps (12) and 13) of FIG. 3 (detailed in FIGS. 4 and 5). An image signal is converted into a digital signal by means of the A/D converter 21. The signal is then subjected to such image processing as noise removal by the processor 22 and stored into the image memory 23. The image stored in the image memory 23 is read out onto the display through the processor 22 and, at the same time, subjected to the defect classification. For achieving the defect classification, such software functions for extracting image information to detect the pattern contour, detecting the portion at which the detected image and the reference image differ from each other, determining the continuity between the differing portion and the contour, and calculating the size of the differing portion are incorporated in the processor 22. Of course, the reference image is stored in the memory within the processor.

After the determination of the existence of the defect at the specified point to be inspected and the defect classification have been finished, the result of the classification is overwritten on the specified point to be inspected on the wafer map and also stored in an inspection data base. In this way, inspection of one point is completed.

If other points still remain to be inspected, the point to be inspected next is specified on the wafer map and the steps of procedure of FIG. 3 subsequent to the specification of the point to be inspected are repeatedly performed for each of the points to be inspected. When the inspection of the wafer has been entirely finished, the density of all the defects/the defects classified by type/the defects classified by size and the product yield are calculated for each chip and each wafer in step (14). The calculation of the product yield is performed with the use of previously recorded tables of degrees of criticalness against defect sizes for each type of defect. The tables of degrees of criticalness against defect sizes are such that they correlate the defects of protrusion, cavity, pinhole, and isolation classified by size with their respective degrees of criticalness. The results of such calculation, together with the results of inspection, are stored in the inspection data base, as shown by step (14), and the data are output therefrom and used according to the need, as shown by step (15). This will be discussed in greater detail below.

If wafers still remain to be inspected in the wafer cassette, the wafer to be inspected next is taken out of the wafer cassette and it is inspected according to the procedure shown in FIG. 3. The density and the yield rate of a plurality of wafers are also calculated correspondingly to the above described case of one wafer.

Figure 6A:
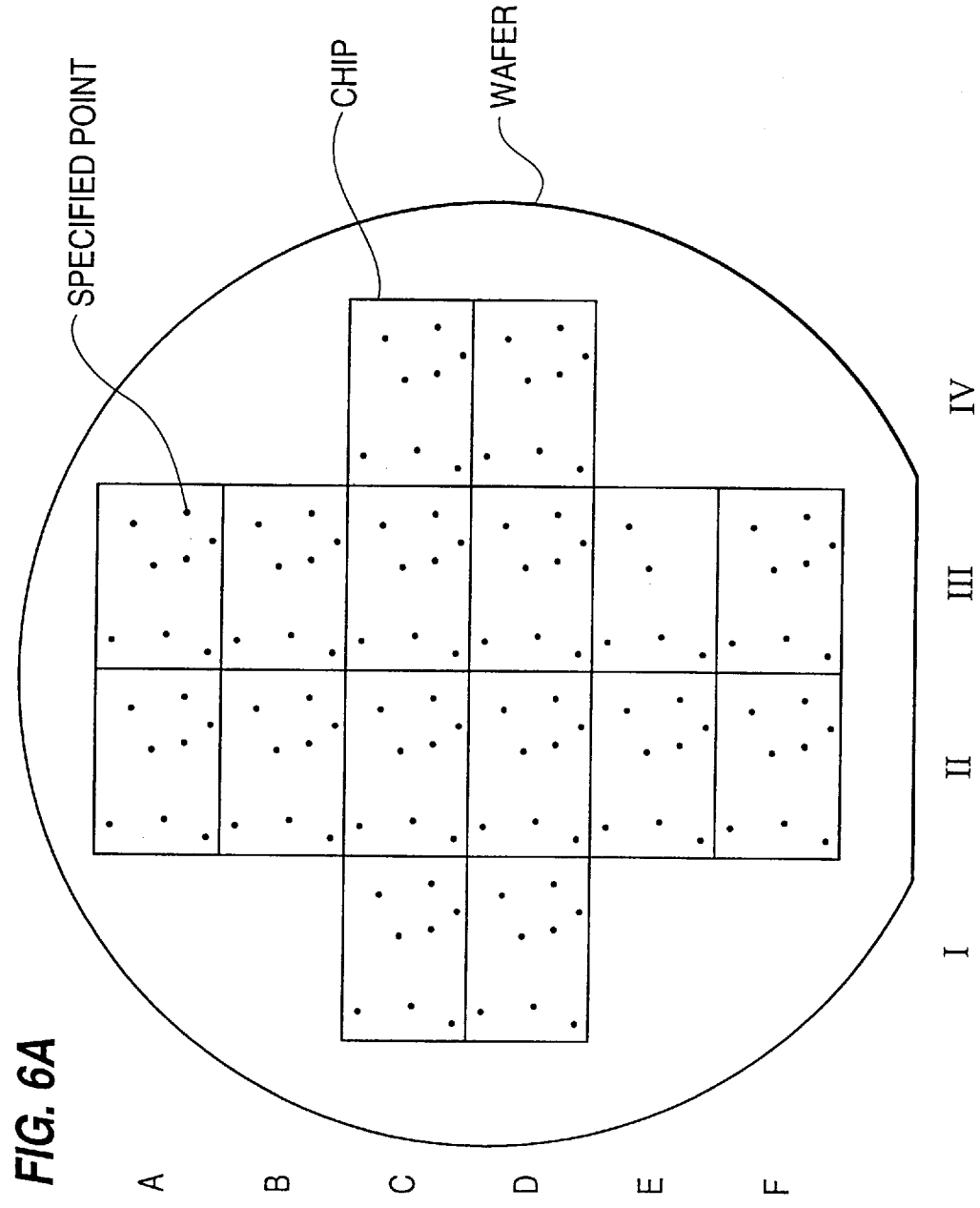

FIG. 6A shows the specified points to be inspected on the wafer map and FIG. 6B shows the result of the defect classification (shown, for example, in FIGS. 4 and 5) overwritten on the specified points to be inspected on the wafer map. Here, the size of defects such as a protrusion and a cavity are normalized with the minimum pattern width and the minimum pattern space. The size of the defects are classified into three category such as less than a third ($1/3$), from a third ($1/3$) to two-thirds ($2/3$), and more than two-thirds ($2/3$) of the space. In the example shown in FIG. 6B, two chips, AII (line A, column II) and AIII (line A, column III), have already been classified, while other chips are not classified yet.

The result of the defect classification may be described in the classification table shown in FIG. 7 instead of the wafer map. The respective densities of defects (i.e., a number of defects detected relative to the number of points inspected) are obtained for each wafer and/or each chip based on the amount of data. FIG. 7 shows an example of calculation of the density of defects within a chip and of the density of each type of defect within a wafer. The result of calculation for each size of the defects also is obtained. If an inspection of the entire wafer is performed instead of the inspection of the specified points to be inspected, the density of the defects for each chip or wafer can be obtained based on the amount of data and the size of the wafer/chip.

Next, correspondence is determined for the classified defects relative to the degree of criticalness (i.e., the probability of the defect being or becoming a killer defect) obtained by manufacturing performance. For instance, a correlation between the degrees of criticalness and protrusion defect size is shown in FIG. 8. The respective degrees of criticalness are correlated with each defect classified by type such that a protrusion defect size less than $1/3$ of the space corresponds to three percent as the degree of criticalness (i.e., a three percent chance that the defect will become a killer defect), a protrusion defect size from $1/3$ to $2/3$ of the space corresponds to forty percent as the degree of criticalness, and a protrusion defect size more than $2/3$ of the space corresponds to seventy percent as the degree of criticalness. These respective degrees of criticalness are used in calculation of a probability of wafer failure or chip failure (the reciprocal of product yield). For example, the probability of chip failure is calculated such that the respective degree of criticalness for each defect which exists within the chip is multiplied by a weight coefficient which is assigned based on the relative degree of criticalness for each defect, and the results of this multiplying are summed as follows:

$$\text{(The probability of failure for chip)} = \sum (\text{weight coefficient for the defect}) \times (\text{respective degree of criticalness for the defect})$$

Figure 9:
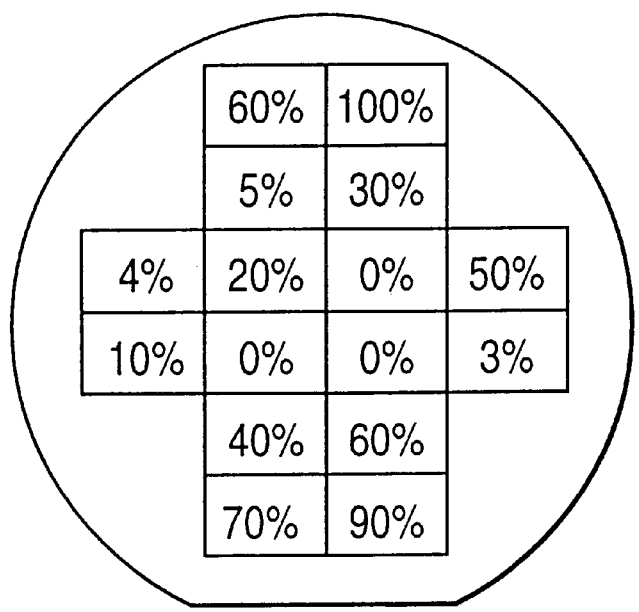
FIG. 9 is a drawing explanatory of displaying the degree of failure calculated in accordance with the present invention.

The weight coefficient of the maximum respective degree of criticalness for a defect within the chip is '1', for example, for definite killer defects such as line breakage or a short circuit, while other weight coefficients are from '0' to '1'. The probability of failure calculated is expressed on the wafer map shown in FIG. 9. The probability of wafer failure is obtained by means of summing all the probabilities of chip failures within the wafer.

In the foregoing, such a method has been described in which determination of existence of a defect and defect classification is started by the operator specifying a point to be examined on the map. Instead of that, an automatic method may be used in which points to be inspected are mechanically approached according to specification given in the recipe and the determination of existence of defects and classification of the defects are mechanically performed.

In the foregoing, such a method has been described in which only predetermined points to be inspected are inspected while the stage is moved in a step and repeat manner. Instead of that, it may be possible to move the stage continuously to have the entire surface of the wafer or a range of it inspected.

When making inspection of the entire surface of the wafer, it is not necessarily required to have the reference image recorded prior to the inspecting operation. It is also possible, during the course of the inspecting operation, to read in the image of a corresponding portion of an adjoining chip or cell and successively record such images as reference images for use.

The capability of additionally recording or re-recording reference images during the course of the inspecting operation is usable also when luminance or contrast of a previously recorded reference image is greatly different from that of the inspected image and it is therefore desired to alter the reference image.

To provide for the case where the luminance or contrast of a previously recorded reference image becomes greatly different from that of an inspected image, it is practicable to design the apparatus such that image parameters such as luminance, saturation, and contrast of the image for inspection and the reference image can be altered separately for the image for inspection and the reference image.

Depending on the specimen, the image can become bad in quality. Even if the differing portions are detected as defects, it sometimes becomes impossible to have them automatically classified. In such a case, it is preferred that a function be provided to automatically give an operator-assist alarm so that the operator can correct the situation.

When a charged particle beam such as an electron beam or an ion beam is used, it sometimes takes a long time to charge up a specimen. The image for positioning or the image for inspection is not utilized until after irradiation of such a charged particle ray has been applied for a predetermined period of time.

Simultaneous display of the inspection SEM image and the reference SEM image is also possible. Hence, the appropriateness of the results of classification can be easily confirmed.

In the foregoing, a method has been described in which a positioning process is performed using a highly magnified image after an alignment process has been performed using a lowly magnified image. However, the apparatus may be provided with a function to directly locate a specified point to be inspected, without making an alignment process beforehand, by searching around the vicinity of the point to be inspected until the point is detected.

In the foregoing, an XY-stage has been used. Instead of the XY-stage, an XYT-stage (where T represents inclination) may be used and, in such a case, the form of a specimen can be inspected in its inclined state.

Only the functions of determining existence of defects in the inspection image and classifying the defects have been described in the foregoing. However, if the apparatus is provided with such an analyzing function as that of a characteristic X-ray analyzer or an Auger electron analyzer, analytical data such as composition of the defective portion can also be obtained.

In the foregoing, an electron beam has been used as the probe for image formation. Instead, an ion beam, an optical beam, or a mechanical probe may be used as the probe.

The case of one probe-one pixel has been described in the foregoing. A system in which images are formed with multiple probes or with multiple pixels may also be used.

In the foregoing, an image obtained by scanning has been used. It is also possible to use an image formed by an image-forming optical system as the object.

The case of inspecting a semiconductor wafer has been described above. The object for inspection may be a wafer for an imaging device, a display device or a semiconductor wafer to be used in other types of equipment. Alternatively, the object for inspection may be of a specimen form other than that of a wafer.

What is claimed is:

1. A method for pattern inspection forming an image of a specimen and inspecting a pattern formed on the specimen, comprising the steps of:

storing a reference image corresponding to an image of said specimen into a memory:

comparing a read out reference image from said memory with said image of said specimen;

detecting differing portions between said reference image and image of said specimen as defects;

classifying said differing portions into a plurality of types with at least distances to an adjacent pattern measured with a minimum space used as a unit;

determining a probability of defect becoming a killer defect of said specimen based on said defects classified by type; and displaying a result of said determination on a display screen, wherein said differing portion and said reference image are overlapped and displayed on said display screen, and said differing portion is shifted to an edge of said adjoining pattern so that said differing portion comes into contact with said edge of said adjacent pattern, whereby said distance between said differing portion and said adjacent pattern is measured based on the distance of the movement.

2. A method for pattern inspection forming an image of a specimen and inspecting a pattern formed on the specimen, comprising the steps of:

storing a reference image corresponding to an image of said specimen into a memory;

comparing a read out reference image from said memory with said image of said specimen;

detecting differing portions between said reference image and image of said specimen as defects;

classifying said differing portions into a plurality of types with at least distances to an adjacent pattern measured with a minimum space used as a unit;

determining a probability of defect becoming a killer defect of said specimen based on said defects classified by type; and displaying a result of said determination on a display screen, wherein said differing portion and said reference image are overlapped and displayed with a predetermined scale on said display screen, whereby a distance between said differing portion and said adjoining pattern is measured by using said scale.

3. A method according to claim 2, wherein said scale is shaped like a straight line, a concurrence of concentric circuits which have an edge of the differing portion as the center of said circles, or a grid line.

* * * * *